United States Patent [19]

Millar et al.

[11] Patent Number: 5,136,062

[45] Date of Patent: Aug. 4, 1992

[54] PREPARATION OF EPOXY NITRATES

[75] Inventors: Ross W. Millar, Saffron Walden; Norman C. Paul, Hoddesdon; Peter Golding, Kings Langley, all of England

[73] Assignee: The Secretary of State for Defence in Her Britannic Majesty's Government of the United Kingdom of Great Britain and Northern Ireland, London, England

[21] Appl. No.: 669,406

[22] PCT Filed: Jul. 14, 1989

[86] PCT No.: PCT/GB89/00813

§ 371 Date: Mar. 22, 1991

§ 102(e) Date: Mar. 22, 1991

[87] PCT Pub. No.: WO90/01029

PCT Pub. Date: Feb. 8, 1990

[30] Foreign Application Priority Data

Jul. 22, 1988 [GB] United Kingdom ............... 8817545

[51] Int. Cl.$^5$ .................. C07D 301/00; C07D 301/16
[52] U.S. Cl. ..................................... 549/513; 549/555
[58] Field of Search ........................................ 549/513

[56] References Cited

U.S. PATENT DOCUMENTS 3,058,994 10/1962 Schrage ............................... 549/510

FOREIGN PATENT DOCUMENTS 687351 5/1964 Canada ................................ 549/510

OTHER PUBLICATIONS

Eremenko et al., Chem. Abstr. vol. 68, No. 9, Feb. 26, 1968, 39373c.

*Primary Examiner*—J. E. Evans
*Attorney, Agent, or Firm*—Nixon & Vanderhye

[57] ABSTRACT

A method of preparing a nitrate ester of an epoxy alcohol, which consists of reacting an epoxy alcohol with $N_2O_5$ in an inert solvent at a temperature of $-10°$ C. to $-40°$ C., followed by quenching the reaction mixture in aqueous solution. Quenching separates the nitric acid and nitrate ester coproducts into aqueous and organic phases respectively to prevent subsequent reaction between the two. Reaction between the nitric acid coproduct and epoxy alcohol reagent to produce acyclic contaminants is supressed by adding the epoxy alcohol to excess $N_2O_5$, thereby rapidly converting available alcohol to nitrate ester.

10 Claims, No Drawings

PREPARATION OF EPOXY NITRATES

This invention relates to a method for the preparation of the nitrate esters of epoxy alcohols, hereinafter also referred to as epoxy nitrates.

Nitrates esters of epoxy alcohols, of which glycidyl nitrate (the nitrate ester of glycidol) is probably the best known example, have known and useful explosive properties and are also useful starting products for the preparation of various polyfunctional compounds.

Epoxy nitrates have in the past been prepared by a general method employing acyclic precursors which are first treated with mixtures of concentrated nitric and sulphuric acids to produce partly nitrated intermediates, after which the intermediates are isolated and purified and are then treated with a base to effect ring closure. Examples of such methods are disclosed in *Will.Ber.-Deutsch Chem.Ges.* 41 1117 (1908) in which the nitration step described is the di-nitration of glycerol, and Petty and Nichols *J.Amer.Chem.Soc.* 76 4385 (1954) in which the nitration step described is the mono-nitration of 3-chloropropane-1,2-diol. Such multiple-step methods are tedious, may result in low yield of the final closed-ring product, and are hazardous because they require the isolation and purification, usually by distillation, of reactive nitrated acyclic intermediates.

More recently, nitrate esters of certain α-epoxy alcohols have been prepared by a single step method, described by L. T. Eremenko and A. M. Korolev, (Izvestiya Akademii Nauk SSSR, Seriya Khimicheskaya 5, 1142-1144 (1967)), which obviates many of the problems associated with the aforementioned multi-step methods. This single step method consists of reacting an α-epoxy alcohol with a 16:26 w/w mixture of 100% nitric acid and acetic anhydride at a temperature of −10° C. for 20 minutes, after having first added the alcohol dropwise to the acid mixture. However, although a high yield of epoxy alcohol is recoverable from the water-quenched reaction mixture (for example a yield of 81% of glycidyl nitrate is reported from glycidol), this method also has several disadvantages.

One disadvantage of the method of Eremenko and Korolev is that is requires the use of an unstable and potentially dangerous nitrating mixture (nitric acid and acetic anhydride) which is known to generate internally the unstable explosive acetyl nitrate. Such mixtures when containing more than 50% by weight of nitric acid in acetic anhydride are especially dangerous, having been shown by T. A. Brown and J. A. C. Watt (Chemistry in Britain 3(11), 504 (1967)) to act as detonating explosives. For safety reasons the content of nitric acid in the mixture must therefore be maintained at considerably below 50% by weight. Since the method of Eremenko and Korolev requires a molar excess of nitric acid (a molar excess of about 60% is reported) to ensure the nitration reaction goes to completion, then this excess has to be matched by an even greater quantity by weight of acetic anhydride. This relatively large quantity of acetic anhydride present in the reaction mixture represents a wasted component, since it does not take part in the primary nitration reaction but is nevertheless consumed, mainly by conversion to acetic acid during the course of the reaction and the subsequent quenching of the reaction mixture in aqueous solution. This in turn creates the problems of disposing large quantities of waste acid.

A further disadvantage of the method of Eremenko and Korolev is that even after several washings with aqueous solutions, the epoxy nitrate products are found to be contaminated with appreciable amounts (2.5% w/w reported) of dinitro acetates.

It is the object of the present invention to provide a method of preparing epoxy nitrates, and particularly nitrate esters of monohydric epoxy alcohols, which obviates at least some of the aforementioned disadvantages. More especially, it is an object of the present invention to provide a one reaction step method for producing nitrate esters of epoxy alcohols which is less hazardous than the aforementioned methods.

According to the present invention, there is provided a method of preparing a nitrate ester of an epoxy alcohol which comprises the steps of (a) reacting, at a temperature of between −10° C. and −70° C., an epoxy alcohol with dinitrogen pentoxide ($N_2O_5$) in an inert organic solvent to produce said nitrate ester and nitric acid, and (b) separating the nitrate ester and nitric acid coproducts.

The present method is capable of producing epoxy nitrates in high yields of more than 80% by weight based on epoxy alcohol, with very little or no coproduction of water-insoluble acyclic nitrate esters and without the use of an explosively-unstable nitrating medium.

The present epoxy nitrates are produced in step (a) by the following exothermic reaction:

where $X(OH)_n$ and $X(ONO_2)_x(OH)_{n-x}$ are the present epoxy alcohol and the present epoxy nitrate, respectively, n is an integer equal to the number of hydroxyl groups present in the epoxy alcohol, and x is an integer less or equal to n and is equal to the number of moles of $N_2O_5$ reacted with each mole of epoxy alcohol. The integer n, and therefore x, is preferably equal to one.

The present inventors have found that this reaction takes place rapidly at below-ambient temperature, and that competing epoxy ring-opening side reactions between the coproducts can be supressed by rapidly separating the coproducts once formed. For this reason the coproducts are preferably separated within 30 minutes of the commencement step (a) when the reaction temperature exceeds −25° C., within 15 minutes of the commencement of step (a) when the reaction temperature exceeds −15° C.

It has also been found that the epoxy groups within the epoxy nitrate coproduct are generally less sensitive than the epoxy groups within the unreacted epoxy alcohol to ring-opening attack by the nitric acid co-product. By maintaining a molar excess of $N_2O_5$ throughout step (a), both during the combination and reaction of the two reagents, unreacted epoxy alcohol is rapidly converted to less sensitive epoxy nitrate before it can react with the nitric acid coproduct. The molar excess of $N_2O_5$ employed in step (a), over that required to react with all hydroxyl groups present in the epoxy alcohol, is preferably from 1% to 50%, more preferably from 5% to 20%. In order to maintain this excess during the combination of the two reagents, the epoxy alcohol is preferably added to the $N_2O_5$ dissolved present in the inert solvent. In order to maintain the temperature of the reaction mixture at or below −10° C., the reaction is preferably cooled during this addition.

The reaction of step (a) is preferably conducted at a temperature of between −10° C. and −40° C., more preferably between −15° C. and −30° C. Low temperatures at or below −10° C. are required because they inhibit ring-opening reactions between the epoxy groups and nitrating agents present in the reaction mixture whilst the relatively fast nitrate ester-forming reaction proceeds. At temperatures below −30° C., the reduced solubility of the products and reagents in the solvent becomes an increasing problem.

The use of low reaction temperatures in the reaction of step (a) is facilitated by conducting the reaction in an inert organic solvent which is liquid at the reaction temperature employed. Examples of suitable solvents are halogenated alkanes such as $C_1$-$C_2$ chloroalkanes, and $C_1$-$C_2$ chlorofluoroalkanes. By the use of such solvents the products and reagents may be diluted in the reaction mixture to suppress the formation of epoxy polymers whose production may be catalysed by the presence of the nitric acid coproduct. This problem tends to increase at higher reaction temperatures. For this reason, preferably sufficient solvent is used to maintain the total concentration of epoxy groups in the reaction mixture at less than 4 mols liter$^{-1}$ of solvent for reaction temperatures above −30° C.

The epoxy alcohol used in the present method will in general comprise an oxirane substituted on one of its two heterocyclic ring carbon atoms by a first monovalent acyclic organic radical substituted by at least one hydroxyl group. The remaining heterocyclic ring carbon atom may be unsubstituted; alternatively it may be substituted by a second monovalent organic radical which may be the same or different to the first organic radical, and which is optionally substituted by one or more hydroxyl groups. Preferred organic radicals are alkyl radicals, especially $C_1$-$C_5$ alkyl groups, substituted by up to two hydroxyl groups. The alcohol is preferably a monohydric (n=1) or dihydric (n=2) epoxy alcohol, and is most preferably a monohydric epoxy alcohol. Preferred epoxy alcohols are hydroxyalkyl-substituted oxiranes, preferably containing from 3 to 25 carbon atoms more preferably from 3 to 10 carbon atoms. Examples of preferred epoxy alcohols, which are preferably used in substantially anhydrous form, are glycidol, 3,4-epoxy butanol, butane-1,2-diol-3,4 epoxide, and butane-1,4 diol-2,3 epoxide.

The dinitrogen pentoxide used in the present method may be prepared by any suitable process, but is preferably prepared by the known reaction of dinitrogen tetroxide with ozone.

Step (b) of the present method preferably comprises quenching the reaction mixture in an aqueous solution, into which nitric acid and any remaining $N_2O_5$ are rapidly transferred to leave the epoxy nitrate in the organic phase. The dilute nitric acid solution thus formed is relatively unreactive towards the epoxy nitrate product remaining in the organic phase. This acidic solution is preferably neutralised with base before the aqueous and organic phase are separated, though the solution may contain the base dissolved therein before quenching commences. This not only helps to remove the final traces of acid from the organic phase, but also produces a salt solution in the aqueous phase which inhibits losses of the water soluble epoxy nitrate product through the aqueous phase when the two phases are separated. Thereafter, the epoxy nitrate product may be recovered from the organic phase.

The present invention will now be described by way of Example only.

MATERIALS

Glycidol (2,3-epoxypropanol; 2-(hydroxymethyl)oxirane) was supplied by Aldrich Chemical Company. It contained up to approximately 25% homopolymer, and was distilled on Kugelrohr before use. Its boiling point was approximately 140° C. at 20 mm Hg pressure.

$N_2O_5$ (Dinitrogen pentoxide) free from nitric acid and lower oxides of nitrogen was prepared by the oxidation of dinitrogen tetroxide ($N_2O_4$) with ozone. In view of the thermal instability of $N_2O_5$, during its preparation a temperature of less than 30° C. and preferably less than 20° C. was employed throughout. All operations were carried out under anhydrous conditions since $N_2O_5$ is readily hydrolysed to nitric acid. An ozone/oxygen mixture, from a commercially available ozoniser was passed into a glass vessel containing $N_2O_4$. Oxidation occured in the gas phase and the resulting $N_2O_5$ was carried in the oxygen stream and trapped in a series of cold traps kept at −78° C. Any unreacted $N_2O_4$ was subsequently reacted by resubliming the initial trapped product in ann ozonised oxygen stream. The colourless white crystals of $N_2O_5$ produced could be stored at −78° C. for at least 7 days before use without any noticeable decomposition, and were found to have a melting point well above room temperature.

Dichloromethane (methylene chloride) was distilled before use from $CaH_2$.

3,4-Epoxybutanol was prepared by epoxidising but-3-en-1-ol (supplied by Fluka Chemicals) with meta-chloroperbenzoic acid under the conditions described by D. J. Pasto and C. Cumbo *J. Org. Chem.* 30, 1271-2 (1965), using tetraglyme as a solvent. It had a boiling point of 77°-78° C. at a pressure of 10 mm Hg, and showed the expected $^1H$ nmr and ir spectra.

Safety Note

The nitration reactions described below were carried out in an armoured cupboard with fume extraction. Solutions of $N_2O_5$ are corrosive so rubber gloves and a face mask were worn when these solutions were handled.

EXAMPLE 1

Preparation of glycidyl nitrate (1,2-epoxy-3-nitratopropane; 2,3-epoxypropanol nitrate)

A nitration apparatus consisting of a 500 ml flange-top flask equipped with mechanical stirrer, thermometer, drying tube and dropping funnel was assembled. The flask was charged with an anhydrous solution of $N_2O_5$ (61.5 g, 0.57 mol) in dichloromethane (300 ml) and the stirred. The mixture was chilled below −25° C. by means of an external cardice-acetone bath. At the onset of $N_2O_5$ crystallisation, an anhydrous mixture of glycidol (42.2 g, 0.57 mol) in dichloromethane (50 ml) was added in a rapid stream with vigorous stirring while the flask temperature was held below −20° C. by addition of cardice to the cooling bath (temperature −55° to −60° C). Addition took 8 minutes. The initially precipitated $N_2O_5$ redissolved giving a clear solution.

After the end of the addition, the reaction mixture was stirred for a further 4 minutes at −25° C. (bath temperature −35° C.), then tipped into ice water (500 ml) in a large separating funnel and immediately neutralised by addition of solid sodium hydrogen carbonate (Indicator test). The lower, organic layer was then separated and set aside whilst the upper, aqueous layer was washed with dichloromethane (200 ml) which had been used to rinse out the reaction flask, separated, and the organic extracts combined. The combined extracts were then washed with brine (150 to 200 ml), the organic layer separated and the brine was extracted with further dichloromethane (150 to 200 ml). The combined extracts were then dried over anhydrous magnesium sulphate (about 20 g), in a stoppered conical flask, for at least 1 hour (but preferably overnight) and then finally the solvent was removed under reduced pressure on a Rotavapor at 30° C./150 mm Hg. Excessive vacuum and/or temperature was avoided to reduce losses of the relatively volatile product, and because it further constituted an explosion hazard.

The yield of product was 58 g (85%). $^1$H nmr, infrared (i.r.) and high pressure liquid chromatography (hplc) analysis identified the product as glycidyl nitrate containing 0.5% nitroglycerine.

Product Analysis $^1$H nmr: $\delta$(CDCl$^3$) 2.6–3.0 (m, 2H); 3.1–3.4 (m, 1H); 4.15–4.9 (m, 2H). CH$_2$Cl$_2$ signal ($\delta$5.30) should be absent.

i.r.: $\nu_{max}$ (liq. film) 1644* (s; —NO$_2$ asym.); 1282 (s; —NO$_2$ sym.); 968 (m; epoxide (?)**); 861 (s; —NO$_2$ gp)cm$^{-1}$ hplc: RP8 column, acetonitrile-water 60:40/1.5 ml min$^{-1}$/23° C. Detection wavelength: 210 nm. Internal standard for quantitation: dipropylphthalate. Approximately 0.5% nitroglycerine (R$_t$ 210 s.) was found in the glycidyl nitrate (R$_t$ 185s) product.

* This peak was broad (1632–1656 cm$^{-1}$) ** Or 998 (m) or 909 (m) cm$^{-1}$.

EXAMPLE 2

Preparation of 3,4-epoxybutanol nitrate

To a mixture of N$_2$O$_5$ (5.54 g, 51.3 m mol) in dichloromethane (30 ml) chilled below $-25°$ C. in a reaction vessel, was added 3,4-epoxybutanol (4.49 g, 51 mmol) in dichloromethane (5 ml). The latter was added in a rapid stream with vigorous mixing while the temperature of the resulting mixture was maintained below $-20°$ C. by the addition of cardice to a cooling bath surrounding the vessel. The reaction mixture was stirred for 4 minutes after which the resulting epoxy nitrate product was recovered using the same procedure described under Example 1 but with approximately one-tenth of the quantity of materials used therein. This recovery procedure yielded 6.35 g (93%) of a colourless oil, which was identified as 3,4-epoxybutanol nitrate from its $^1$H nmr and i.r. spectra. Its purity was checked by hplc, which showed a single peak.

Product Analysis $^1$H nmr: $\delta$(CDCl$_3$) 1.8–3.2 (m, 4H); 3.3–3.9 (m, 1H); 4.60 (t, 2H).

i.r.: $\nu_{max}$ (liq.film) 1632 (s, —NO$_2$ asym.); 1282 (s, —NO$_2$ sym.); 982 (m, epoxide(?)**; 879/854 (s, —NO$_2$ gp) cm$^{-1}$.

hplc: RP8 column, acetonitrile-water 60:40/1.75 ml min$^{-1}$/25° C. Detection wavelength: 210 nm. R$_t$(epoxy nitrate) 131 s.

** Or 1002 (m) or 962 (m) cm$^{-1}$.

We claim:

1. A method of preparing a nitrate ester of an epoxy alcohol by the nitration of an epoxy alcohol, comprising the steps of:
   (a) adding an epoxy alcohol to a solution of dinitrogen pentoxide (N$_2$O$_5$) in an inert organic solvent to form a reaction mixture, maintained at a temperature of between $-10°$ C. and $-70°$ C., in which said nitrate ester and nitric acid are formed as products, the total amount of N$_2$O$_5$ used in the reaction mixture being not greater than 50% more than that required to react with all of the hydroxyl groups present in the added epoxy alcohol, and
   (b) separating the nitrate ester and nitric acid components.

2. A method according to claim 1 wherein the reaction of step (a) is conducted at a temperature of between $-10°$ C. and $-40°$ C.

3. A method according to claim 1 wherein a molar excess of N$_2$O$_5$ is employed in step (a).

4. A method according to claim 3 wherein the molar excess of N$_2$O$_5$, over that required to react with all the hydroxyl groups present in the epoxy alcohol, is between 1% and 50%.

5. A method according to claim 1 wherein the nitrate ester and nitric acid coproducts are separated within 30 minutes of the commencement of step (a) when the reaction temperature exceeds $-25°$ C., and within 15 minutes of the commencement of step (a) when the reaction temperature exceeds $-15°$ C.

6. A method according to claim 1 wherein the N$_2$O$_5$ is dissolved in the solvent prior to step (a).

7. A method according to claim 1 wherein the concentration of epoxy groups in the solvent is maintained at less than 4 mols liter$^{-1}$ when the reaction temperature is more than $-30°$ C.

8. A method according to claim 1 wherein step (b) comprises quenching the reaction mixture in an aqueous solution to form an aqueous phase containing the nitric acid coproduct and an organic phase containing the nitrate ester coproduct.

9. A method according to claim 8 characterised by the further step of adding base to the aqueous phase to at least partly neutralise the nitric acid coproduct transferred thereto from the organic phase.

10. A method according to claim 8 wherein the aqueous solution contains a base dissolved therein to at least partly neutralise the nitric acid coproduct.

* * * * *